United States Patent [19]

DiGangi et al.

[11] Patent Number: 4,852,592
[45] Date of Patent: Aug. 1, 1989

[54] APPARATUS FOR THE CLEANING OF CONTACT LENSES

[75] Inventors: Joel D. DiGangi, San Diego, Calif.; Kenneth L. Ross, Redmond, Wash.

[73] Assignee: Digangi and Ross, San Diego, Calif.

[21] Appl. No.: 235,994

[22] Filed: Aug. 23, 1988

Related U.S. Application Data

[63] Continuation-in-part of Ser. No. 84,945, Aug. 13, 1987, abandoned.

[51] Int. Cl.⁴ .......................... B08B 3/04; B08B 11/02
[52] U.S. Cl. .................................... 134/57 R; 134/98; 134/99; 134/113; 134/140; 134/155; 134/158; 206/5.1
[58] Field of Search .................. 134/57 R, 95, 98, 99, 134/107, 140, 143, 147, 149, 155, 158, 162, 184, 186, 113; 206/5.1

[56] References Cited

U.S. PATENT DOCUMENTS

| | | | |
|---|---|---|---|
| 2,886,046 | 5/1959 | Du Gal | 134/58 R |
| 3,438,317 | 4/1979 | Merolli et al. | 134/95 |
| 3,621,855 | 11/1971 | Rabinowitz | 134/57 R |
| 3,623,492 | 11/1971 | Frantz et al. | 134/143 |
| 3,690,333 | 9/1972 | Kierner | 134/95 |
| 3,871,395 | 3/1975 | Murry | 134/107 |
| 3,997,049 | 12/1976 | Sherman | 206/5.1 |
| 4,011,941 | 3/1977 | Parsons | 206/5.1 |
| 4,409,999 | 10/1983 | Pedziwiatr | 134/95 |
| 4,582,076 | 4/1986 | Prat | 134/57 R |

Primary Examiner—Philip R. Coe
Attorney, Agent, or Firm—Thomas Schneck

[57] ABSTRACT

A contact lens washer having a plurality of disposable solution containers for sequential cleaning cycles using daily cleaning solution, enzymatic, solution, disinfecting solution and saline/neutralizing solution. The containers are inserted into the contact lens washer in an inverted condition. A plurality of liquid released solenoids cause the solution containers to inject liquid into a cleaning chamber having a pair of contact lenses to be cleaned. The contact lenses are encased in a lens-encasing member which is agitated to enhance the cleaning capabilities of the contact lens washer. A timing cycle module provides sequential fluid supply both to and from the cleaning chamber and controls agitation of the lens-encasing member.

20 Claims, 5 Drawing Sheets

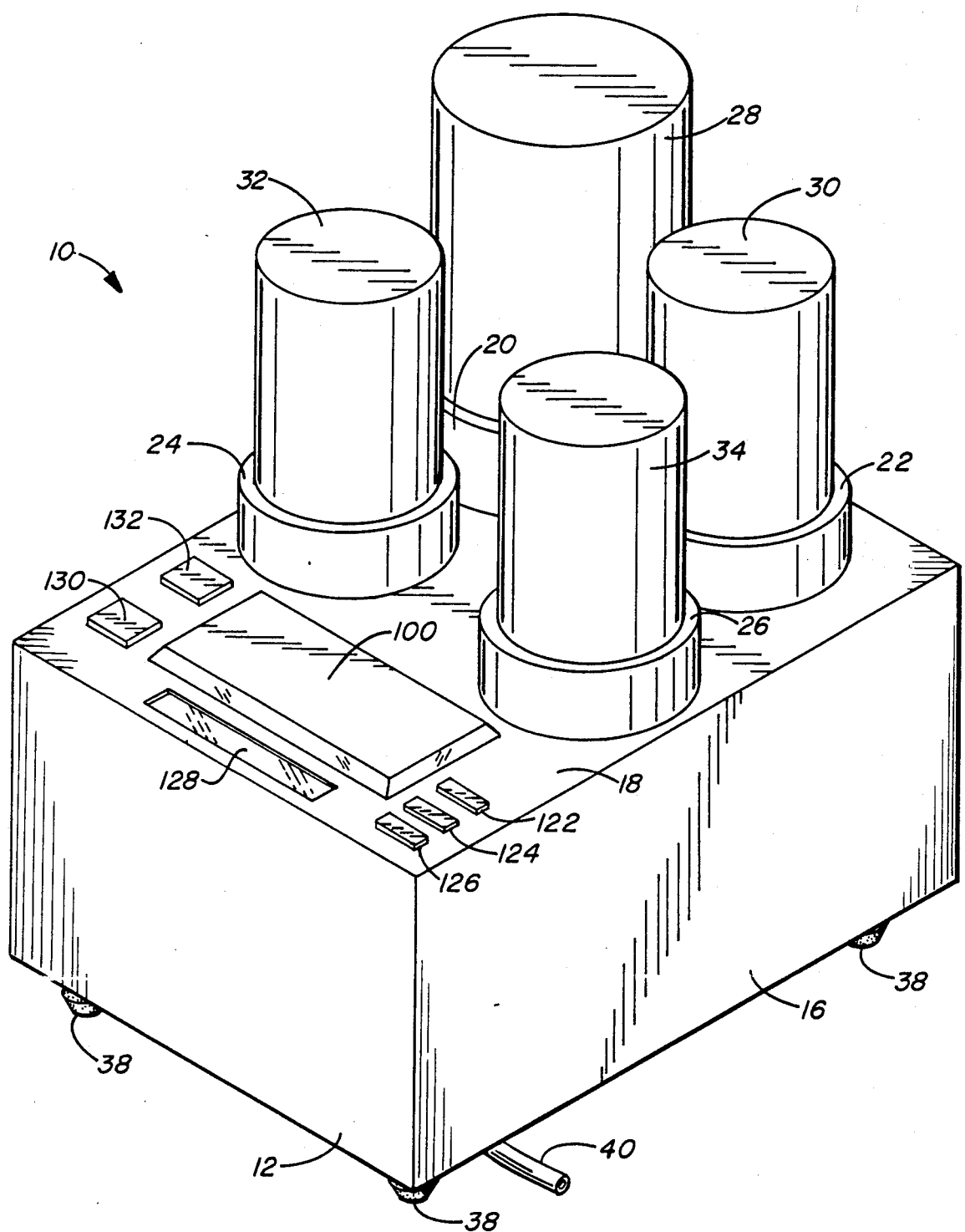
FIG._1.

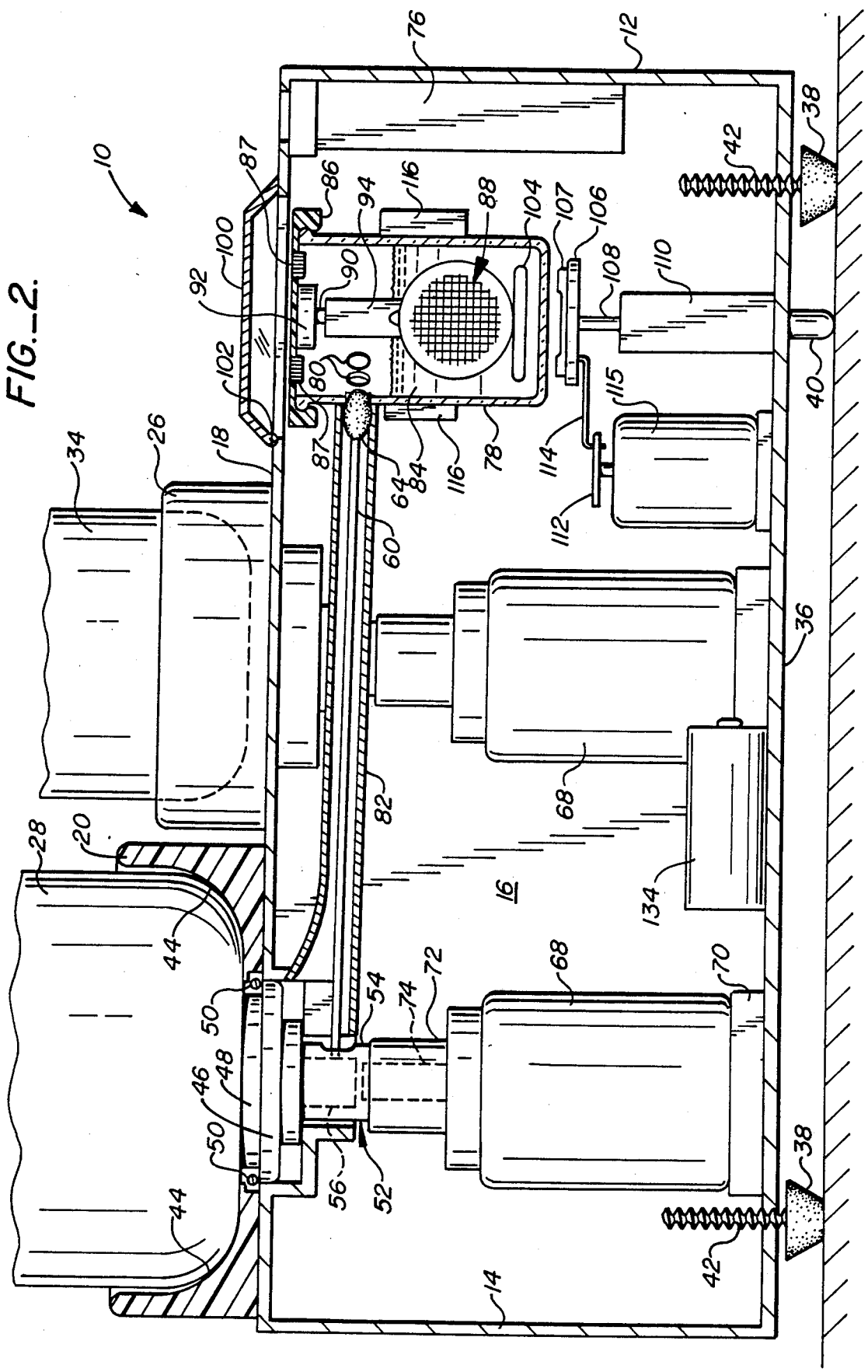

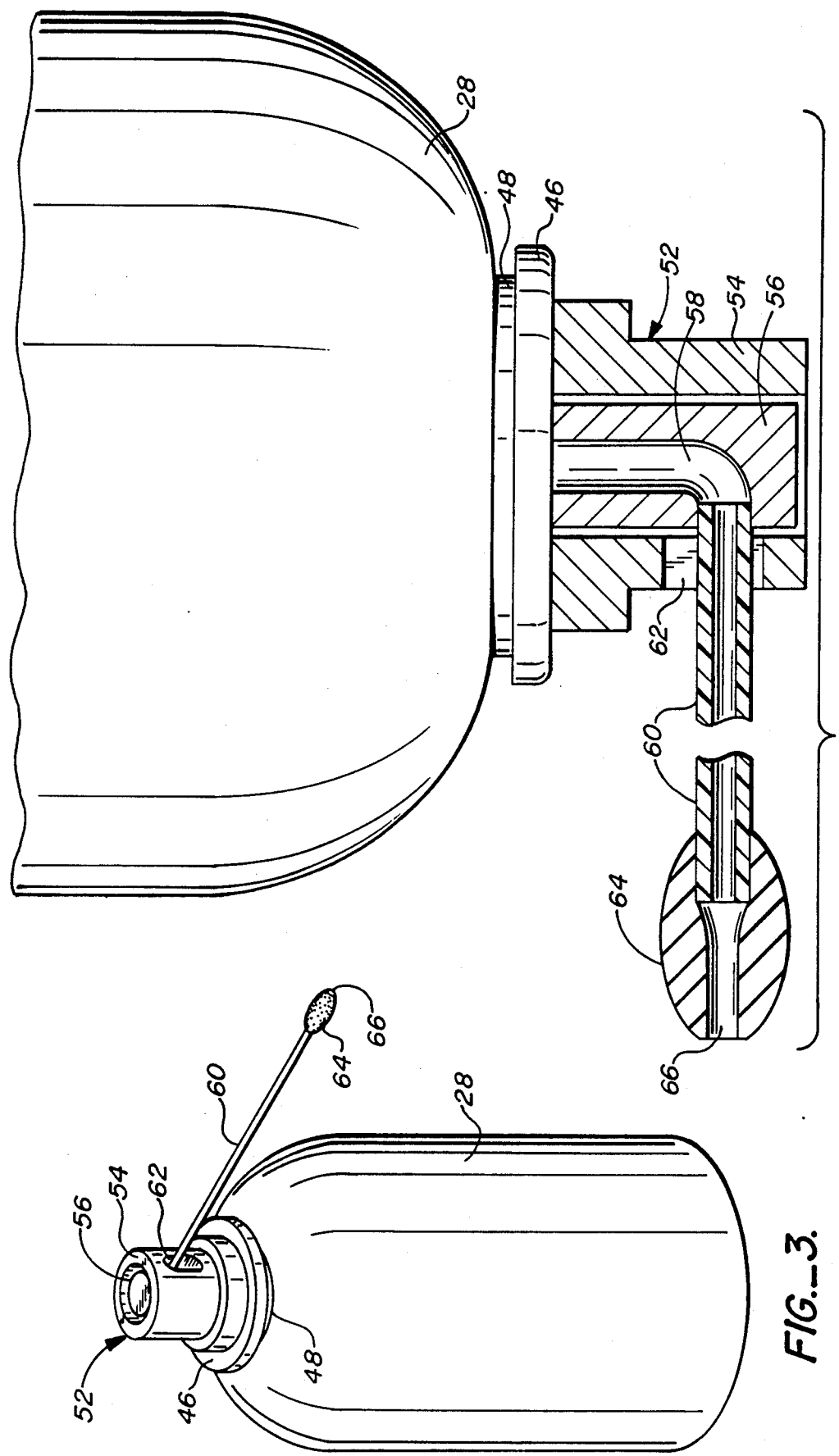

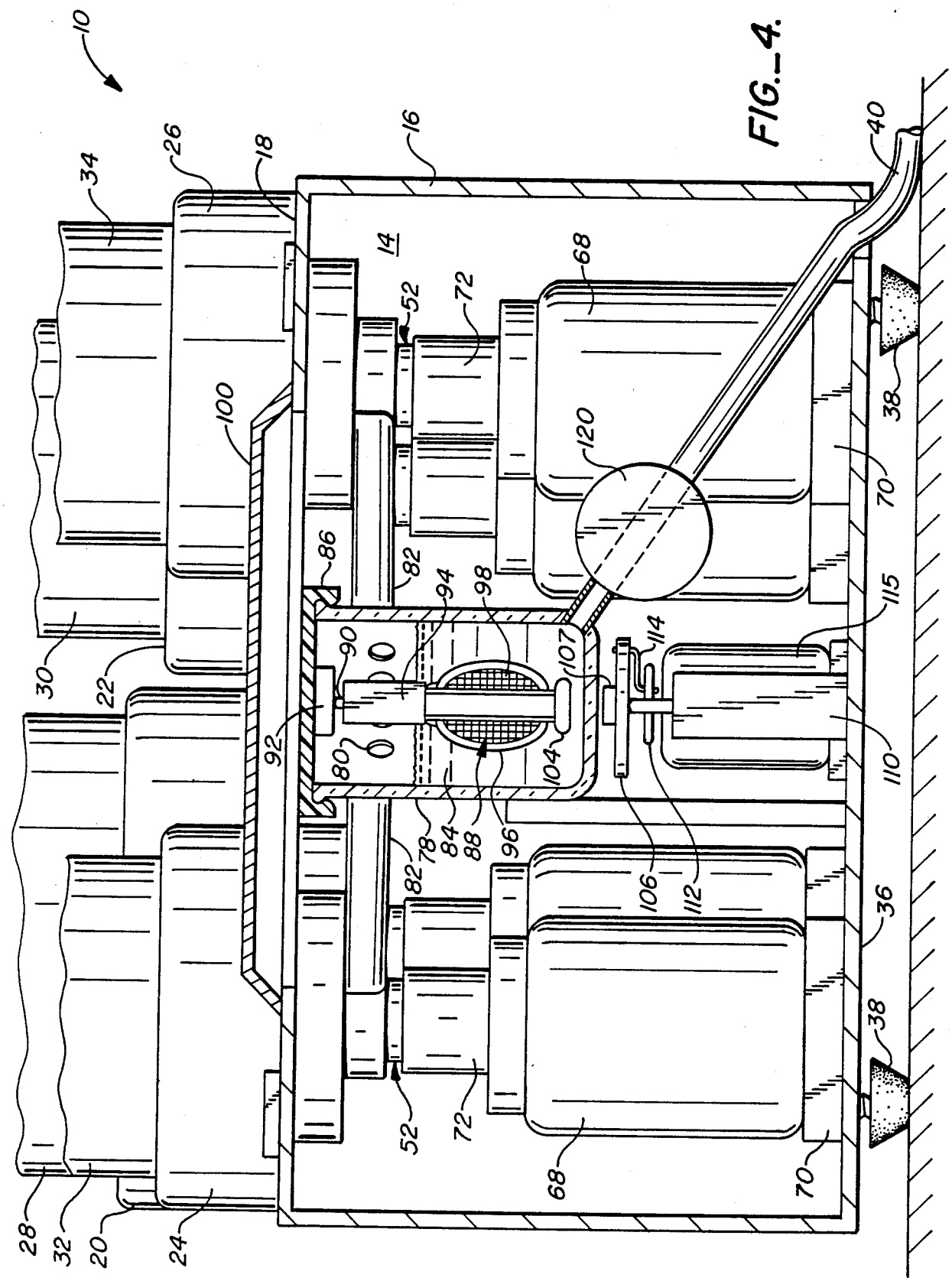

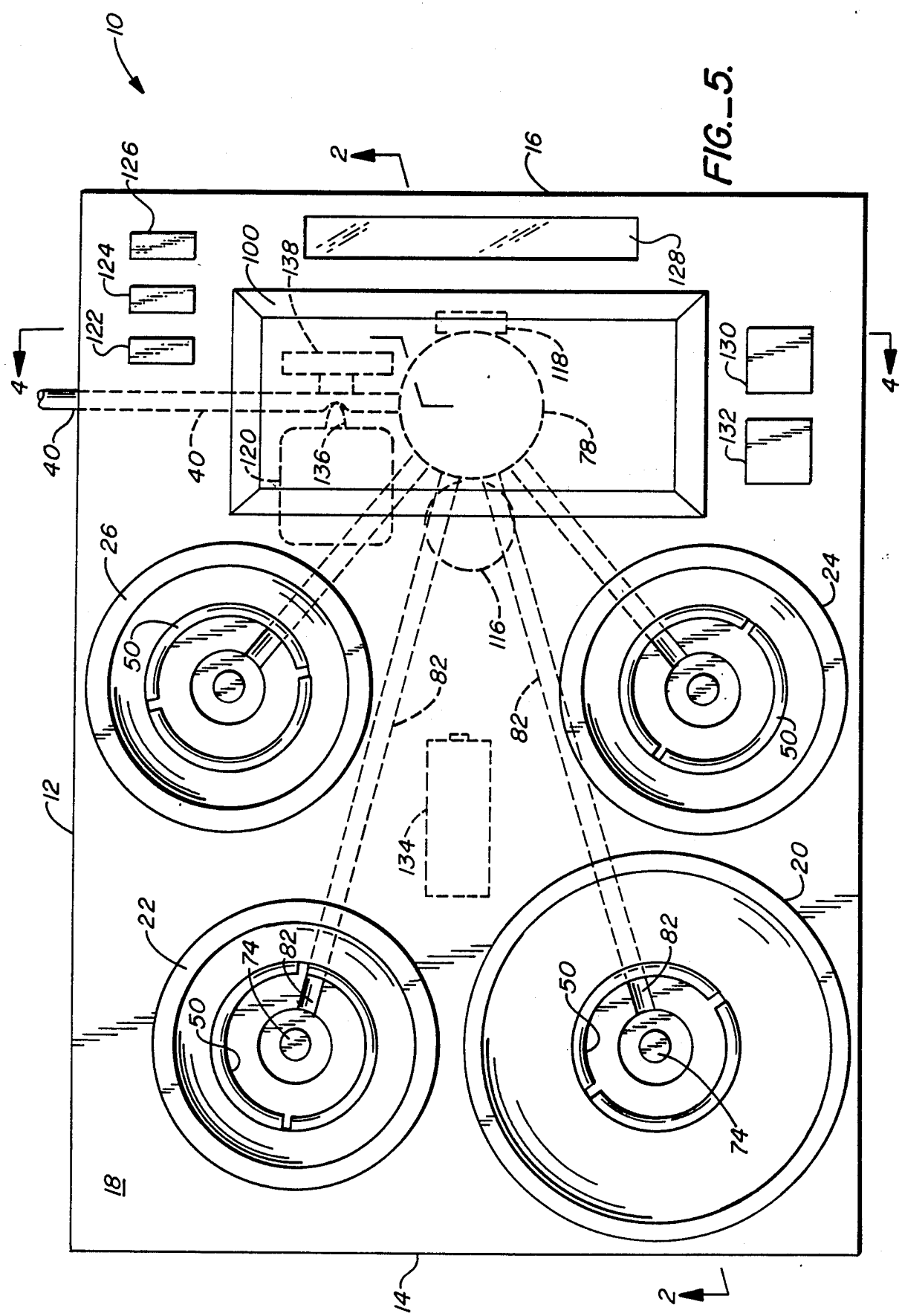
FIG._5.

APPARATUS FOR THE CLEANING OF CONTACT LENSES

CROSS REFERENCE TO RELATED APPLICATION

The present application is a continuation-in-part of application Ser. No. 084,975, filed Aug. 13, 1987 and now abandoned.

1. Technical Field

The present invention relates generally to contact lens care and particularly to apparatus for care of contact lenses.

2. Background Art

While soft contact lenses have added greatly to the comfort and convenience of corrected vision, the lenses are hydrophilic and as a result must be cleaned and disinfected regularly to prevent bacterial contamination To date, contact lens deposits are recognized as the most serious of problems to be overcome by lens care regimens. Soft contact lenses allow for growth of bacteria present in the eye and consequently may cause serious eye infection if bacterial growth is not prevented.

Two methods of sterilizing hydrophilic contact lenses are currently in practice. The thermal care method requires raising contact lenses to a high temperature to destroy any bacteria. Thermal sterilization devices are in use, but have been known to change the chemical composition of soft lenses, rendering them unwearable. Moreover, such devices accomplish no surfactant cleaning. The second method for sterilizing contact lenses is by non-thermal, or chemical, treatment. Nonthermal treatment requires manually placing the lenses in a disinfectant for a period of time, typically ten to fifteen minutes, to carry out the sterilization process.

Generally, the disinfectant utilized in non-thermal treatment is a solution, such as hydrogen peroxide, which is injurious to the eye. Thus, after removal from the disinfectant, the contact lenses must be soaked in a neutralizing solution for some amount of time.

In addition to being susceptible to bacterial contamination, hydrophilic lenses permit accumulation of protein, lipid, mucin, and other deposits. Protein deposits cause irritation of the eye as well as fogging and blearing of vision. Deposits accumulate to the point where lenses lose their transparency and may cause wearers to experience conjunctivitis. Thus, at least once a week, contact lenses must be soaked in an enzymatic solution which removes the deposits. The enzymatic cleaning may be done before or after the lenses are sterilized.

A typical weekly procedure, including enzymatic cleaning, involves: (1) a hand washing of the individual lenses with a daily surfactant cleaner by rubbing the lenses with fingers together to remove surface deposits, (2) followed by a two-hour enzymatic cleaning, (3) and a fifteen-minute bath in a disinfecting solution, (4) followed by a six-hour soaking in a saline solution containing a neutralizing platinum disk, or some other available efficacious neutralizing method. Preferably, the contact lenses are hand rinsed prior to insertion into each solution and prior to placement into the eyes of the wearer.

The above-described procedure requires a lens wearer to recurringly attend to the process of cleaning. Additionally, the procedure requires repeated handling of the soft contact lenses which are susceptible to scratches, tears and wear. Each hand cleaning induces a stress on the lens which over a period of time adversely affects the properties of the lens.

Devices which sterilize soft contact lenses are known. U.S. Pat. No. 4,582,076 to Prat teaches an apparatus which thermally cleans and sterilizes soft contact lenses in a lens holder. The lens holder is filled with a cleaning liquid and then rotated. After a predetermined period of time the apparatus emits a sound, whereafter the user must empty the lens holder of the cleaning liquid and fill the holder with a sterilizing liquid. Again, the apparatus emits a sound after a predetermined time to signal the end of the sterilizing process. The apparatus reduces the physical handling during the two-step process of cleaning and sterilization.

U.S. Pat. Nos. 3,621,855 to Rabinowitz and 3,623,492 to Frantz et al. teach containers to hold washing fluid and lens cages to receive contact lenses for insertion into the washing fluid. The lens cages are then agitated. Like the Prat apparatus, the devices of Rabinowitz and Frantz et al. require the attention of a user to move the contact lenses from the first solution to a second solution U.S. Pat. No. 4,381,285 to Wittenberg, however, includes a striker arm which moves a lens holder from one solution storage container to a second storage container. The Wittenberg patent teaches automatic relocation of contact lenses from a sterilizing solution which is injurious to the eyes into a soaking solution which neutralizes any sterilizing solution remaining on the contact lenses. The device reduces the inconvenience of applying various solutions to contact lenses, and consequently encourages daily sterilization. However, the Wittenberg device eliminates only a few steps in the weekly procedure involved in the enzymatic cleaning and sterilization of contact lenses.

Moreover, the above-mentioned devices require that the users personally pour the various liquids into the devices. Such handling of the liquids jeopardizes the success of the sterilization process.

It is an object of the present invention to provide an apparatus for the care of contact lenses which accomplishes all of the procedural steps involved in the surface and enzymatic cleaning and the sterilization of the contact lenses with a minimal amount of physical handling of the solutions and the contact lenses.

DISCLOSURE OF THE INVENTION

The above object has been met by an apparatus having orderly sequential cleaning cycles of "daily cleaning solution with surfactant", enzymatic solution, disinfecting solution and saline/neutralizing solution, with application of the various solutions to contact lenses being performed by a purely mechanical process. Preferably, the solutions are within disposable containers that are inserted onto the apparatus. The present invention eliminates much of the inconvenience involved in periodic cleaning of a contact lens, thereby promoting proper care.

The "daily cleaning with surfactant", enzymatic, disinfecting and saline/neutralizing solutions are stored within containers which each have a nozzle that releases a quantity of solution when depressed. The containers are each connected to a cleaning chamber by a plurality of two passageways. The containers are inserted into the apparatus in an inverted state. Depression of the nozzles is provided by solenoids having plungers which move vertically to contact the center of the multi-element nozzle. The containers may be in gravity-feed relation to the cleaning chamber, but preferably the containers are pressurized and inject a specific amount of solution into the cleaning chamber with each depression. The containers are "disposable" in the sense that they are not refilled by a consumer.

A perforated lens-encasing member is rotatably disposed for fluid contact with the fluid in the cleaning chamber. The lens-encasing member is bifurcated to hold a pair of contacts in spaced-apart relation to each other. A permanent magnet is fixed to the lens-encasing member. At the exterior of the cleaning chamber, is a motor driven magnet which is driven in a reciprocating rotational manner. The two magnets are in magnetic coupling relation so that the lens-encasing member is likewise oscillated.

A timing cycle circuit provides orderly sequential fluid supply to the cleaning chamber, as well as fluid evacuation after each cycle. Moreover, the timing cycle circuit controls the motor for oscillating the lens-encasing member. It is possible to choose any of three or more contact lens cleaning cycles. The particular cycles depend upon a number of factors, the most important of which is the type of contact lenses. The present invention may be used with soft and hard contact lenses, as well as gas permeable lenses and the like.

An advantage of the present invention is that it permits a user to insert a pair of contact lenses into the apparatus which then self-actingly provides a daily surface cleansing, an enzymatic cleaning, sterilization and a saline/neutralizing rinse. A wearer need not handle the contact lenses between successive steps in the procedure. Moreover, because these solutions are mechanically injected into the apparatus, contamination by wearer handling of the solutions is precluded. The various cycles are affected by a pre-programmed sequence so that the cleaning regimen is simplified and use-compliance with prescribed practices is enhanced. Another advantage is that the agitation of the contact lenses reduces the time needed to achieve a desired degree of cleanliness, as the mechanical rotation provides a superior surface cleaning. An additional advantage is that a sufficient rinsing of the harsh cleaning fluids is ensured, thereby eliminating the occurrence of painful eye irritation resulting from an improperly rinsed lens.

BRIEF DESCRIPTION OF THE DRAWINGS

FIG. 1 is a perspective view of a contact lens washer in accord with the present invention.

FIG. 2 is a side sectional view of the washer of FIG. 1.

FIG. 3 is a perspective view of a solution container of FIG. 1.

FIG. 3A is an inverted sectional view of the outlet portion of the solution container of FIG. 3.

FIG. 4 is a front sectional view of the washer of FIG. 2.

FIG. 5 is a top view of the washer of FIG. 4.

BEST MODE FOR CARRYING OUT THE INVENTION

Referring to FIGS. 1 and 2, a contact lens washer 10 includes a front panel 12, a back panel 14, and opposed side panels 16. The contact lens washer 10 also includes a cover plate 18 having a plurality of container receptacles 20, 22, 24 and 26.

Container receptacles 20–26 support solution containers which are supplied with the liquid required for regular contact lens cleaning. For example, container 28 may be filled with a saline/neutralizing solution which is primarily saline solution. Container 30 has a daily cleaner which is a surfactant in the non-thermal treatment of hydrophilic contact lenses. Container 32 may be filled with an enzymatic solution for periodic removal of protein and other deposits, while container 34 has a disinfecting solution. As will be described more fully below, the solution containers 28–34 may either be pressurized or adapted for gravity feed of liquid. On operation, the types of solutions depend upon the type of lenses to be cleaned.

As best seen in FIG. 2, a base plate 36 of the contact lens washer 10 receives a number of adjustable feet 38. Rotation of a foot 38 at a corner of the base plate 36 affects the level of that corner relative to the remaining corners. In this manner, the contact lens washer 10 may be adjusted to assure proper height of the apparatus for flow through a solution discharge tube 40 into a sink or the like. Each foot 38 is fixed to a threaded member 42 which is received within an internally threaded hole in the base plate 36. Thus, rotation of an adjustable foot 38 changes the height of the base plate relative to the adjustable foot. The contact lens washer may also include structure, such as a slotted panel, which permits, the washer to be suspended from a wall.

Referring now to FIGS. 2, 3 and 3A, the solution containers, such as the container of saline/neutralizing solution 28, are secured in an inverted position. The solution container 28 has an arcuate portion which is received within the associated container receptacle 20. A support surface 44 of the container receptacle is likewise arcuate to accommodate the shape of the solution container 28. The mass of the solution container rests upon the support surface 44. A lip section is spaced apart from the solution containing portion of the container so as to provide a recessed area 48. When placed in position in the contact lens washer 10, the recessed area 48 acts as a bearing surface for a spring-lock ring 50. The spring-lock ring may be made of either a metallic or an elastomeric material. If metallic, the springlock ring includes a slit therethrough. A force which is along the axis of the solution container 28 does not dislodge the container. However, a force on the container which includes a component other than along the axis of the container does cause dislodgement. Thus, depression of the nozzle 52 of the solution container will not work to remove the solution container from position within the contact lens washer, but the container may be removed when desired. Alternatively, the springlock ring may be of the type which provides a securing force which is sufficient to maintain the position of the container during normal operation, but releases the solution container when the container is subjected to the upward pull of a user.

The solution containers are shown to be four in number. However, this number is not critical. It may be possible to combine two solutions into a single container and reduce the number of containers. On the other hand, innovations in the art of contact lens manufacturing any provide lenses which are an improvement when compared to conventional contact lenses, but which require additional lens care solutions. Additional container receptacles may be provided in the contact lens washer.

The solution container of saline/neutralizing solution, along with the other solution containers, may be metallic or may be made of a plastic material. In either case, the containers should be disposable. By "disposable containers" what is meant is that the containers are not to be refilled by a user. The solution containers are preferably recyclable. However, the containers should not be opened by a user. In this manner, application of a sterilized solution to a pair of hydrophilic contact lenses in insured. Solution need not be handled or poured by a user. Instead, solution containers are periodically changed.

The nozzle 52 of a solution container 28 includes a stationary outer segment 54 and a depressible inner segment 56. The inner segment includes an axial bore 58. An axial force on the depressible inner segment releases solution from the container 28 into the axial bore 58. A plastic tubing 60 passes through a cutaway area 62 of the stationary outer segment 54 and is selectively received within the bore 58. At the end of the plastic tubing is a fitting 64 having at least one bore 66 for release of solution.

Referring particularly to claim 2, liquid release solenoids 68 are shown. A solenoid 68 rests upon a mounting 70 and like the solution container nozzle 52, includes a stationary outer member 72 and a vertically movable member 74. The vertically movable member 74 is a plunger, shown in phantom.

The stationary outer segment 54 of the nozzle 52 is in frictional contact with the stationary outer member 72 of the liquid release solenoid 68. Thus, the solenoid aids in positionally stabilizing the solution container 28. Each solution container of a contact lens washer 10 is associated with a liquid release solenoid, so that, at least in the illustrated embodiment of the present invention, the solenoids are four in number. Attached to the front panel 12 of the contact lens washer 10 is a module 76 of timing cycle circuitry which provides orderly sequential operation of the liquid release solenoids, as well as other functions such as an automatic cycle counter, and fluid level sensor of the washer.

Upon release of liquid from a solution container, the liquid is channeled through the tubing 60 and is released from the opening of the fitting 64. The tip of the tubing has a frustroconical shape to insure a proper seating into an feeder port of a cleaning chamber 78. It is important that there be no gap between the fitting 64 and the cleaning chamber 78. Sterilization is jeopardized if gaps permit the entrance of unfiltered air or foreign particles into the cleaning chamber from the feeder port. As shown in FIG. 2, the cleaning chamber 78 includes a plurality of other feeder ports 80 for the seating of fittings, not shown, from the remainder of the solution containers.

During insertion of a solution container a conduit 82 guides the fitting 64 and tubing 60 in the direction of the proper cleaning chamber feeder port. The end of the conduit opposite the cleaning chamber is flared to facilitate insertion, since the tubing 60 must bend during insertion.

Referring to FIGS. 2 and 4, the cleaning chamber 78 is typically made of a hard plastic and is capable of retaining a solution 84. A snap-fit or twist-on cap 86 is removably placed on the cleaning chamber. The cap includes a microbial filter 87 to filter foreign particles and allow clean air to enter and exit the cleaning chamber during filling and draining cycles. A bifurcated lens-encasing member 88 is suspended from the cap 86 for fluid contact with a solution in the cleaning chamber. A shaft 90 is rotatably fixed to a bearing member 92 to permit rotation of the lens-encasing member 88 within the solution 84. An upright support 94 is fixed to the shaft 90. A pair of lens cages 96 and 98 is connected to the upright shaft at hinges. The lens cages are commonly known in the art and have a truncated semispherical member and a cover member. Each semispherical member is perforated at a planar surface and is hinged to the cover member. The cover member also includes perforations and has a clasp which binds the semispherical member and the cover member when clasped. "Perforations" is understood to include any means of insuring even fluid flow over the encased contact lenses in the cleaning chamber. After containment of a pair of lenses, the lens cages are brought to a face-to-face position and inserted into the cleaning chamber.

The cleaning chamber 78, the cap 86 and the lens-encasing member 88 combine to form what is referred to as a lens-runner assembly. Directly above the lens-runner assembly is a lid which is fixed to the cover plate 18 at a hinge 102, shown in FIG. 2. By pressing to open the lid 100, a user is provided access to the lens-runner assembly for removal of the cap and lens-encasing member from the cleaning chamber. Once removed from the cleaning chamber a pair of contact lenses may be removed from or inserted into the lens cages 96 and 98.

At the lower extremity of the lens-encasing member 88 is a permanent magnet 104. The permanent magnetic is magnetically coupled to a drive magnet 107 embedded within a fly wheel 106 disposed below the cleaning chamber 78. Alternatively, the drive magnet may be fixed to the upper surface of the fly wheel 106. The fly wheel is axially fixed to a support shaft 108 which is freely rotatable relative to a bearing housing 110. The support shaft 108 and the bearing housing 110 function merely to permit free rotation of the fly wheel 106 and its supported drive magnet 107.

The freely rotatable fly wheel 106 is controlled by a motor driven fly wheel 112, with the fly wheels being linked by a connecting rod 114. A motor 115 rotates the motor-driven fly wheel 112, but because of the linkage the dependent fly wheel 106 does not fully rotate. Instead, the dependent fly wheel 106 is caused to oscillate. The connecting rod 114 turns the dependent fly wheel slightly less than 180 degrees, after which the direction is reversed.

Thus, a reciprocating rotational motion of the fly wheel 106 and its supported drive magnet 107 is produced. The magnetic coupling to the permanent magnet 104 fixed to the lens-encasing member 88 causes concurrent motion of the lens-encasing member. Alternately a gear drive assembly may be attached to the cap at the cleaning chamber to accomplish the same agitation. This agitation of contact lenses within a solution contained by the cleaning chamber is preferred to the spinning action typical of contact lens washers. Agitation is more effective in cleaning and rinsing of the contact lenses, since the agitation is less susceptible to the adverse effects of centrifugal force upon the contact lenses and the lens care solution within the cleaning chamber.

At the outer surface of the cleaning chamber 78 is a fluid level sensor 116. The fluid level sensor may be of the electric eye type, having a light emitting diode at one side and a light sensing member at the opposite side. The sensing device is positioned to determine whether there is an overabundance or an insufficient amount of liquid within the cleaning chamber. If an improper amount is detected, the cycle is stopped and a warning device is used to notify a user. The warning device may be a flashing light, for example, and should indicate to the user that the particular solution container has been emptied, or that some such problem is present.

Referring again to FIG. 4, a solution is evacuated from the cleaning chamber 78 via the solution discharge tube 40. An electrically controlled pinch valve 120 regulates fluid flow through the discharge tube. The pinch valve 120, like the fluid release solenoids, is initiated by the timing cycle circuitry.

The operation of the contact lens washer 10 will be described with reference to FIGS. 1 and 5. The timing cycle circuitry causes the contact lens washer 10 to sequentially progress through the cycles which in the past have required the recurring attention of a contact lens wearer. Three program selectors 122, 124 and 126 are shown and enable a user to choose one of three programmed cleaning procedures. For each of the three cycles, the user is informed of the progress by means of a read-out display 128 which indicates the lapsed time.

A contact lens wearer must firstly lift the lid 100 for insertion of the contact lenses into the cleaning chamber 78. The contact lens washer 10 is then initialized by depression of an on-off switch 130. Beside the on-off switch is a reset switch 132 which permits a user to restart the washer 10 in mid-cycle.

Power for operation of the contact lens washer is received by an electric cord, not shown. A transformer and converter circuit furnish a direct current for employment of the drive motor, liquid release solenoids, the pinch valve 120, as well as the remainder of the circuitry. Alteratively, power may be received by means of a rechargeable battery 134 which adds to the portability of the washer. The rechargeable battery also functions to prevent memory loss should there be a temporary loss of electrical power to the contact lens washer 10. This is particularly important in case of a mid-cycle power loss.

Depression of the program selector 122 initializes a cleaning and disinfection cycle. Activation of the liquid released solenoid associated with the daily cleaning solution container 32 fills the cleaning chamber 78. The daily cleaning solution includes a surfactant which removes most of the surface mucous, proteins and other "fatty" deposits from contact lenses. Referring briefly to FIG. 2, the motor driven fly wheel 112 is then caused to rotate. The connecting rod 114 linking the motor-driven fly wheel 112 to the dependent fly wheel 106 provides a reciprocating rotational motion to the dependent fly wheel and to the drive magnet 107 mounted thereon. The magnetic coupling of the drive magnet 107 and the permanent magnet 104 causes a concurrent oscillation of the bifurcated lens-encasing member 88. The agitation creates a continuous repositioning of the contact lenses within the cages, thereby insuring that the entire surfaces of the lenses are exposed to the solution. Moreover, the agitation provides mechanical cleaning effects due to the movement of the lenses relative to the solution. The mechanical cleaning effects supplement the chemical cleaning produced by the solution itself.

Returning to FIGS. 1 and 5, after a short period of time, the daily cleaning solution is evacuated from the cleaning chamber 78 via the discharge tube 40. That is, the retractable member 136 of the pinch valve 120 is moved away from the stationary member 138 of the pinch valve to permit the free flow of fluid through the discharge tube 40. The cleaning chamber is then filled with saline/neutralizing solution from container 28 and agitation is again initialized to rinse the cleaning chamber, whereafter the pinch valve 120 again evacuates the solution.

The next step in the daily cleansing process is to channel the disinfectant from the solution container 34 into the cleaning chamber 78. Typically, the solution containers 28-34 are pressurized cans. Activation of a liquid release solenoid presses the plunger 74 of the solenoid into the nozzle of the associated solution container so as to release an amount of solution. The contact lens washer 10 accounts for each release of liquid from each solution container. In this manner, the washer may be programmed to indicate to a user the amount of solution remaining in each of the containers 28-34. The structure of the contact lens washer 10 also permits gravity feed of solution into the cleaning chamber 78. Thus, in the place of the pressurized solution containers, disposable gravity feed containers may be substituted. In such case, however, air ports should be provided within the solution containers. Anti-bacterial membrane filters should cover the vacuum-releasing air ports. The membrane filters permit the passage of air, but prevent the passage of bacteria, much like the filters used in intravenous feedings.

The disinfecting solution from the container 34 is typically hydrogen peroxide. Again, the contact lenses are agitated within the solution. After a programmed amount of time, agitation is ceased and the cleaning chamber 78 is evacuated. The cleaning chamber is then filled with the saline/neutralizing solution and after the contact lenses are permitted to soak, the lenses are ready for wear.

Depression of the second of the program selectors 124 begins an enzymatic cleansing process. The cleaning chamber 78 is filled with saline/neutralizing solution from the container 28 and the lenses are agitated to loosen surface matter on the lenses. The saline/neutralizing solution is then evacuated and the cleaning chamber is filled with enzymatic solution from the solution container 32. Again, the drive motor is activated to agitate the contact lenses. After a preprogrammed period of agitation, the lenses are allowed to soak in the enzymatic solution for approximately another preprogrammed period to allow full cleaning. Programmed periods depend on the type and manufacture of the solutions used in each container. It may be possible to combine two or more of the solutions. As a last step, the enzymatic solution is evaluated and the cleaning chamber is again filled with saline/neutralizing solution.

Periodically, contact lenses undergo a weekly cleaning procedure. Depression of the last program selector 126 initializes such a procedure. The procedure begins with a surface cleaning of the contacts with a combination of daily cleaning solution and saline. The contact lenses are agitated and after a programmed amount of time the solutions are evacuated. The cleaning chamber 78 is rinsed with the saline/neutralizing solution, whereafter the pinch valve 120 releases to evacuate the solution. Enzymatic cleaning of the contact lenses follows. The cleaning chamber is again emptied and rinsed and the disinfecting solution is caused to flow into contact with the contact lenses. This is followed by the disinfecting cycle which extends for a preprogrammed amount of time.

A problem with contact lens wear results from the fact that the disinfecting solution typically includes hydrogen peroxide which is injurious to the eyes. Therefore, any residue fluid on the contact lenses must be neutralized. In a manual regimen of contact lens care, a wearer is instructed to soak disinfected lenses in saline solution within a canister having a neutralizing platinum disk or other neutralizing medium. It has been discovered, however, that saline solution alone, if exposed to the disinfected contact lenses for a sufficient period of time, and with the proper agitation, will have the effect of reducing the hydrogen peroxide levels to the levels achieved by other neutralizing processes. For this reason, it is not necessary to include platinum disks within the saline solution. Preferably, however, the solution container 28 is a combination of saline solution and a neutralizing agent. In such case, neutralization of the hydrogen peroxide is insured and in a much shorter period of time.

As may be seen in FIG. 5, the spring-lock rings 50 which secure the solution containers in position are slotted metallic rings, with each ring comprising two arcuate members. The two arcuate members of a ring are spring biased into the position shown in FIG. 5. However, the force on a ring is such that the ring is permitted to recede into the contact lens washer 10 when a user applies pressure during insertion or removal of a solution container. Because each cycle of a cleaning procedure is followed by a saline/neutralizing rinse, the container receptacle 20 associated with the saline/neutralizing solution container is larger volumetrically than the other three container receptacles 20-24. For example, the solution container of saline/neutralizing solution may be a twelve-ounce container, while the remaining containers are eight ounce by size.

The sequence of cycles outlined above is preferred. However, it is understood that the present invention may be programmed to rearrange the sequence cycles. Moreover, the present invention may be modified for use with "hard" contact lenses, gas permeable lenses or any other such lenses which must be chemically cared for on a regular basis.

I claim:

1. A contact lens washer comprising,
   a housing having a plurality of container receptacles, each having a support surface contoured to releasably receive a container of contact lens care solution and having means for selectively securing said container in a fixed position,
   a plurality of conduits, each of said container receptacles being associated with one of said conduits to channel fluid flow from said containers,
   a cleaning chamber mounted in said housing, said cleaning chamber being in fluid communication with said conduits,
   a flow regulation means for initiating fluid flow from each of said containers,
   means for draining fluid from said cleaning chamber,
   a perforated lens-encasing member disposed within said cleaning chamber, said lens-encasing member having two compartments, each compartment adapted to hold a contact lens,
   motor means for providing relative motion between said lens-encasing member and said cleaning chamber, and
   a timing cycle means for self-operation of said contact lens washer, said timing cycle means controlling said flow regulation means for sequential fluid supply from said containers to said cleaning chamber, said timing cycle means further controlling said motor means and said means for draining fluid from the cleaning chamber.

2. The contact lens washer of claim 1 wherein said support surfaces of the container receptacles are each concave relative to a horizontal plane tangential to the apex of the support surface.

3. The contact lens washer of claim 1 wherein said lens-encasing member is rotatably disposed within said cleaning chamber and wherein said motor means is in communication with said lens-encasing member to provide a reciprocating rotational motion thereto.

4. The contact lens washer of claim 1 wherein said container receptacles are four in number to receive pressurized containers of saline/neutralizing solution, daily cleaning solution, disinfecting solution and enzymatic solution.

5. The contact lens washer of claim 1 further comprising means for sensing the levels of fluid in said cleaning chamber and in said containers and for indicating said levels.

6. The contact lens washer of claim 1 wherein said flow regulation means includes a plurality of solenoids, each solenoid associated with a container receptacle.

7. The contact lens washing of claim 1 wherein said motor means is magnetically coupled to said lens-encasing member to provide said relative motion.

8. A contact lens washer comprising,
   a housing having a plurality of cavities in the upper portion thereof, the contour of a cavity defined by a container support surface,
   a plurality of contact lens care disposable containers, each having an outlet inserted into one of said cavities of the housing, the portion of each disposable container proximate said outlet having a shape corresponding to the contour of the associated container support surface,
   a cleaning chamber mounted in said housing, said cleaning chamber adapted to be filled with a fluid,
   flow regulation means for channeling fluid from a selected disposable container to said cleaning chamber,
   drain means for evacuating fluid from said cleaning chamber,
   a lens-encasing member rotatably disposed within said cleaning chamber, said lens-encasing member having compartments to support a pair of contact lenses in spaced-apart relation and in fluid contact with fluid in said cleaning chamber,
   a motor drive means for rotating said lens-encasing member relative to said cleaning chamber, and
   a timing cycle means for automatically controlling said flow regulation means, said drain means and said motor drive means.

9. The contact lens washer of claim 8 wherein said disposable containers include a saline/neutralizing solution container, a daily cleaning solution container, a disinfectant solution container and an enzymatic solution container, said contact lens washer further comprising means for determining and indicating the fluid levels in said disposable containers.

10. The contact lens washer of claim 8 wherein said disposable containers are pressurized cans, each having a disposable nozzle outlet and tubing extending from said nozzle outlet to said cleaning chamber.

11. The contact lens washer of claim 10 wherein said nozzle outlet has a fixed annular exterior and a depressible interior within the inside diameter of said annular exterior.

12. The contact lens washer of claim 10 wherein said flow regulation means includes a plurality of solenoids, each depressible nozzle being associated with a solenoid.

13. The contact lens cleaner of claim 10 wherein said tubing extending from each nozzle outlet has a tip having a conical shape, the cleaning chamber having apertures to receive in a sealing manner portion of said conically shaped tip.

14. The contact lens washer of claim 8 wherein said motor drive means includes a motor assembly and first and second ferromagnetic members, said motor assembly linked to said first ferromagnetic member for providing reciprocating rotational motion thereto, said second ferromagnetic member being fixed to said lens-encasing member and being magnetically coupled to said first ferromagnetic member for reciprocating rotational motion therewith.

15. The contact lens cleaner of claim 8 wherein said contour of each cavity is concave relative to a horizontal plane tangential to the apex of the container support surface of said cavity.

16. A contact lens washer comprising,
 a plurality of pressurized containers, including a saline/neutralizing solution container, a daily cleaning solution container, a disinfectant solution container and an enzymatic solution container, each pressurized container having a nozzle outlet,
 means for maintaining said pressurized containers in fixed positions,
 fluid transfer means for initiating sequential flow from said pressurized containers via said nozzle outlets,
 a cleaning chamber in fluid communication with said fluid transfer means to receive said sequential flow,
 drain means for evacuating fluid from said cleaning chamber,
 a bifurcated lens-encasing member removable and rotatably disposed within said cleaning chamber, said lens-encasing member adapted to hold a pair of contact lenses in spaced-apart relation to each other and in fluid contact with fluid in said cleaning chamber,
 motor means for rotating said lens-encasing member relative to said cleaning chamber, and
 a timing cycle means for fluid supply to said cleaning chamber and for control of said drain means and motor means.

17. The contact lens washer of claim 16 wherein said timing cycle means includes circuitry for permitting selection of a plurality of cleaning cycles affecting different of said pressurized containers.

18. The contact lens washer of claim 16 wherein said fluid transfer means includes a plurality of solenoids disposed to depress said nozzle outlets.

19. The contact lens washer of claim 16 wherein said drain means includes a pinch valve.

20. The contact lens washer of claim 16 wherein said motor means provides reciprocating rotational motion to said lens-encasing member.

* * * * *

UNITED STATES PATENT AND TRADEMARK OFFICE
CERTIFICATE OF CORRECTION

PATENT NO. : 4,852,592

DATED : August 1, 1989

INVENTOR(S) : Joel D. DiGangi et al.

It is certified that error appears in the above-identified patent and that said Letters Patent is hereby corrected as shown below:

Title page:

Item [63], "Ser. No. 84,945," should read -- Ser. No. 84,975, --.

Item [57] Abstract, line 3, "enzymatic, solution," should read -- enzymatic solution, --.

Column 2, lines 21-22, "a second solution U.S. Pat. No." should read -- a second solution. U.S. Pat. No. --.

Column 11, line 6, "in a sealing manner portion" should read -- in a sealing manner a portion --.

Signed and Sealed this

Nineteenth Day of March, 1991

Attest:

HARRY F. MANBECK, JR.

*Attesting Officer*  *Commissioner of Patents and Trademarks*